United States Patent [19]

Clark et al.

[11] Patent Number: 5,622,734
[45] Date of Patent: Apr. 22, 1997

[54] APPARATUS FOR PRODUCING A CRIMP-BONDED FIBROUS CELLULOSIC LAMINATE

[75] Inventors: Harry E. Clark, Cumming, Ga.; Cynthia W. Henderson, Neenah; Robert C. Marcinek, Appleton, both of Wis.; Frances W. Mayfield, Marietta, Ga.; Thad W. Perkins, Roswell, Ga.; Jorg F. Voss, Roswell, Ga.

[73] Assignee: Kimberly-Clark Corporation, Neenah, Wis.

[21] Appl. No.: 449,380

[22] Filed: May 23, 1995

Related U.S. Application Data

[62] Division of Ser. No. 212,537, Mar. 14, 1994, Pat. No. 5,543,202.

[51] Int. Cl.⁶ ..................................................... B28B 3/10
[52] U.S. Cl. ..................... 425/517; 425/342.1; 425/385; 425/344; 425/503; 425/521; 57/11; 57/114; 57/127.5; 57/351; 72/207; 72/214; 72/252; 199/74; 162/296; 162/361
[58] Field of Search ..................................... 162/296, 361, 162/662, 409, 903; 57/11, 351, 21, 90, 97, 114, 127.5; 72/207, 214, 74, 223, 225, 226, 252.5, 199; 199/74; 425/503, 517, 521, 223, 341.1, 343, 385, 388, 394

[56] References Cited

U.S. PATENT DOCUMENTS

| | | | |
|---|---|---|---|
| D. 242,579 | 11/1976 | Walbrun | D59/2 B |
| D. 262,747 | 1/1982 | Erickson | D59/2 B |
| D. 267,907 | 2/1983 | Schulz | D59/2 B |
| D. 268,961 | 5/1983 | Erickson | D59/2 B |
| D. 287,433 | 12/1986 | Ellers | D5/53 |
| D. 288,150 | 2/1987 | Schulz et al. | D5/53 |
| D. 296,769 | 7/1988 | Schtatz | D5/53 |
| D. 298,586 | 11/1988 | Drew et al. | D5/53 |
| D. 298,587 | 11/1988 | Peddada | D5/53 |
| D. 298,588 | 11/1988 | Peddada | D5/53 |
| D. 298,589 | 11/1988 | Drew et al. | D5/53 |

(List continued on next page.)

FOREIGN PATENT DOCUMENTS

| | | |
|---|---|---|
| 367999A2 | 5/1990 | European Pat. Off. . |
| 370972A1 | 5/1990 | European Pat. Off. . |
| 476976A1 | 3/1992 | European Pat. Off. . |
| 0498623 | 8/1992 | European Pat. Off. . |
| 1586511 | 2/1970 | France . |
| 1059746 | 2/1967 | United Kingdom . |
| 1122431 | 8/1968 | United Kingdom . |
| 1420139 | 1/1976 | United Kingdom . |

OTHER PUBLICATIONS

*The Dictionary of Paper*, 4th ed., American paper Institute, Inc., New York, 1980, pp. 160–161.

Gary A. Smook, *Handbook for Pulp & Paper Technolgists*, 2nd ed., Angus Wilde Publications, Bellingham, Washington, 1992, p. 346.

J. Newell Stephenson, *Manufacture & Testing of Paper and Board*, vol. 3, Pulp and Paper Manufacture Series, McGraw–Hill Book Company, Inc., 1953, pp. 718–722.

*Primary Examiner*—Merrick Dixon
*Attorney, Agent, or Firm*—Karl V. Sidor

[57] ABSTRACT

Disclosed is a process for producing a crimp-bonded fibrous cellulosic laminate. The process includes the steps of: 1) providing at least two superposed plies of a fibrous cellulosic material; 2) passing the superposed plies through a crimp roll arrangement including a rotating crimp element and a rotating anvil element; and 3) applying a pressure load against the rotating elements sufficient to crimp bond the fibrous cellulosic material plies into a laminate. The crimp element has protruding members configured in a discontinuous pattern aligned on an axis that is parallel to the cross-machine direction to provide a substantially continuous uniform area of localized surface contacts between the rotating crimp and anvil elements across the width of the plies. Also disclosed is an overall crimp-bonded fibrous cellulosic laminate and an apparatus for crimp-bonding multiple superposed plies of a fibrous cellulosic material.

20 Claims, 8 Drawing Sheets

U.S. PATENT DOCUMENTS

| | | | |
|---|---|---|---|
| D. 298,590 | 11/1988 | Drew et al. | D5/53 |
| D. 298,701 | 11/1988 | Drew | D5/53 |
| D. 298,702 | 11/1988 | Drew | D5/53 |
| D. 305,181 | 12/1989 | Veith | D5/53 |
| D. 305,182 | 12/1989 | Peddada et al. | D5/53 |
| D. 315,990 | 4/1991 | Blenke et al. | D5/26 |
| D. 318,572 | 7/1991 | Schultz et al. | D5/53 |
| D. 319,349 | 8/1991 | Schultz et al. | D5/53 |
| D. 319,350 | 8/1991 | Paschke et al. | D5/53 |
| D. 322,173 | 12/1991 | Schultz et al. | D5/53 |
| D. 331,665 | 12/1992 | Underhill | D5/53 |
| D. 332,874 | 2/1993 | Shufelt et al. | D5/53 |
| D. 332,875 | 2/1993 | Shufelt et al. | D5/53 |
| D. 332,876 | 2/1993 | Shufelt et al. | D5/53 |
| 728,828 | 5/1903 | Arkell | 428/183 |
| 1,201,701 | 10/1916 | Crane | 5/53 |
| 1,771,983 | 7/1930 | Wandel | 428/43 |
| 1,774,497 | 8/1930 | Wandel | 428/43 |
| 1,954,965 | 4/1934 | Thode | 93/1 |
| 2,020,668 | 11/1935 | Wandel | 428/84 |
| 2,591,359 | 4/1952 | Joa | 154/29 |
| 2,825,117 | 3/1958 | Evans et al. | 26/69 |
| 2,834,809 | 7/1958 | Schutte et al. | 92/3 |
| 3,074,324 | 1/1963 | Nobbe . | |
| 3,106,139 | 10/1963 | Leopoldi | 93/1.1 |
| 3,323,983 | 6/1967 | Palmer et al. | 162/362 |
| 3,377,224 | 4/1968 | Creshan et al. . | |
| 3,556,907 | 1/1971 | Nystrand | 156/470 |
| 3,714,685 | 2/1973 | Yarber | 28/1.2 |
| 3,738,905 | 6/1973 | Thomas | 161/127 |
| 3,834,286 | 9/1974 | Nystrand | 93/1.1 |
| 3,867,872 | 2/1975 | Nystrand | 93/1.1 |
| 4,376,671 | 3/1983 | Schulz | 156/549 |
| 4,659,608 | 4/1987 | Schulz | 428/171 |
| 4,662,042 | 5/1987 | Bayliss, Sr. | 28/269 |
| 4,759,967 | 7/1988 | Bauernfeind | 428/154 |
| 4,978,565 | 12/1990 | Pigneul et al. | 428/156 |
| 5,096,527 | 3/1992 | Biagiotti . | |
| 5,139,841 | 8/1992 | Makouri et al. | 428/109 |
| 5,277,761 | 1/1994 | Van Phan et al. | 162/109 |
| 5,294,475 | 3/1994 | McNeil | 428/154 |

APPARATUS FOR PRODUCING A CRIMP-BONDED FIBROUS CELLULOSIC LAMINATE

This application is a divisional of application Ser. No. 08/212,537 entitled "Process for Producing a Crimp-Bonded Fibrous Cellulosic Laminate" and filed in the U.S. Patent and Trademark Office on Mar. 14, 1994, now U.S. Pat. No. 5,543,202.

FIELD OF THE INVENTION

The field of the present invention is directed toward a process for making multiple ply fibrous cellulosic materials. The present invention is also directed to multiple ply fibrous cellulosic materials.

BACKGROUND OF THE INVENTION

Fibrous cellulosic material such as paper tissue may be composed of a single ply or multiple plies. Secure attachment of plies in a multiple ply material poses problems. One problem associated with multiple-ply tissue products is that the plies can separate while being pulled from a roll. Such separation is particularly inconvenient when a multiple-ply product such as, for example, multiple-ply bathroom tissue is used in institutional multi-roll dispensers which are locked to prevent tampering with the tissue rolls. Separated plies of tissue may become caught in the locked dispenser causing jams or other problems.

In the past, plies have been attached by methods which rely on, for example, adhesive bonding, certain forms of crimp-bonding and/or hydrogen bonding (also called "paper" bonding). Conventional adhesives may be unsuitable for some tissue products and may add expense. Hydrogen bonding which may be created by applying water onto tissue plies can be difficult to adapt to some high-speed manufacturing processes and may produce an unsatisfactory product. Conventional mechanical crimp-bonding techniques (i.e., linear edge crimping) utilize pressure loaded, relatively narrow, hardened-metal patterned crimp wheels and smooth, hardened-metal anvil wheels to create autohesive attachment between plies at the bond points (i.e., attachment between the constituent material of the plies without application of adhesive agents).

Crimp-bonding is created when superposed plies are subjected to relatively high pressures at the bond point. Conventional crimp-bonding processes utilizing crimping wheels and anvil rolls have generally been limited to producing continuous linear bond patterns. These linear bond patterns are usually located along one or both edges of a laminate joining the plies. Conventional crimp-bonding processes are poorly suited for joining plies of material having large widths because bonding is limited to a generally continuous linear configuration intended to be near the edges of a finished sheet. Such a limitation presents a problem because high-speed multiple ply tissue manufacturing processes utilize increasingly wider rolls of material to improve efficiency. For example, some processes employ rolls of tissue having widths over 10 feet.

Simply setting up an array of conventional crimping wheels and anvil wheels across a wide sheet is unsatisfactory. Crimping wheels must be accurately spaced and the linear crimp-bond patterns must maintain their spacing during continuous commercial operation, otherwise the crimp-ponds on the finished product will be misaligned when the wide sheet is slit or cut into smaller widths (i.e., the crimp-bonds would no longer be at the edges of the finished product).

Crimp-bonding processes are quite different from conventional embossing processes. Embossing conveys tissue sheets through the nip created by a hard metal pattern roll and a resilient rubber roll. Alternatively, a set of pattern-matched, intermeshing steel embossing rolls may be used. Such combinations of rolls produce deep, durable indentations in the tissue sheet. Robust bonding between plies as produced by crimp-bonding processes are usually absent. Attachment of the embossed plies, if any, may be accomplished with an adhesive. In some situations, the folding, crinkling or creasing at the embossments may provide limited ply attachment. Conventionally embossed multiple-ply tissue products generally have greater bulk and reduced physical properties (i.e., tensile strength) than a laminate of un-embossed tissue. Moreover, rolls of such bulky embossed products need unacceptably large diameters to provide desired volumes of product for many commercial applications.

Thus, a need exists for a practical process for making a fibrous cellulosic laminate having desirable levels of ply attachment. This need also extends to a practical process for making a crimped-bonded fibrous cellulosic laminate which also has acceptable bulk properties and softness without sacrificing physical strength. Meeting this need is important since it is economically desirable to adapt high-speed manufacturing processes to take advantage of efficiencies created by processing relatively wide rolls of tissue laminates.

There is also a need for an absorbent multiple-ply tissue laminate having desirable levels of ply attachment resulting from crimp-bonding produced without the use of adhesives. This need also extends to such an absorbent multiple-ply laminate which also has acceptable bulk properties and softness. For example, there is a need for a multiple-ply bathroom tissue having desirable levels of ply attachment, good bulk properties and softness as well as desirable delivery of a volume of product when wound into a roll. Meeting these needs are important since it is economically desirable to avoid using adhesives to bond the plies of an absorbent multiple-ply tissue laminate. It is also economically and environmentally desirable to provide rolls of such tissue laminate which can be wound into a standard size roll while providing a commercially acceptable volume of product that has bulk properties, softness and appearance that is acceptable to consumers.

Moreover, there is also a need for an apparatus to produce an absorbent multiple-ply fibrous cellulose laminate having desirable levels of ply attachment resulting from crimp-bonding without the use of adhesives. There is also a need for an apparatus which provides such a laminate product which is robust, avoids destructive vibration or "chattering" and which may readily accept a variety of material widths.

DEFINITIONS

As used herein, the term "adhesion strength" refers to the relative level of bonding between the component layers of a laminate (e.g., a fibrous cellulosic laminate). Unless otherwise specified herein, adhesion strength measurements generally conformed to ASTM Standard Test D 2724.13 and to Method 5951, Federal Test Methods Standard No. 191A, with the following changes: 1) the specimen size is 2 inches by 6 inches (6 inches in the machine direction); 2) the gauge length is set at one inch; and 3) the value of the peak load alone is interpreted as the bond strength of the specimen.

The bond strength of the sample unit is calculated as the average peak load of all the specimens tested. According to the test procedure, each test specimen is composed of a laminate. The layers of the laminate are manually separated for a distance of about 2 inches along the length of the specimen. Samples having more than two layers are tested by placing only the outermost layers in the jaws. Each outer layer is clamped into a jaw of a testing machine and the maximum force (i.e., peak load) needed to completely separate the laminate is measured. The layers are pulled apart at a 180 degree angle. The test equipment jaw travel rate is set at 12 inches per minute. The results of testing (i.e., the adhesion strength) are reported in units of force per unit(s) of width. For example, the adhesion strength can be reported in units of $grams_{force}$ per centimeter (or centimeters) of width; $grams_{force}$ per inch (or inches) of width (e.g., $grams_{force}$ per two inches of width); or other suitable units.

As used herein, the term "crimp-bonding" refers to a form of autohesive bonding between two or more plies of fibrous cellulosic material (i.e., attachment between the constituent material of the plies without application of adhesive agents). Such plies of fibrous cellulosic material may each have a basis weight ranging from about 4 to about 34 grams per square meter. Crimp-bonding is thought to involve two stages: 1) establishing bonding contact between the plies, and 2) bond formation. Bonding contact generally requires relatively high pressure distributed over a small area of the superposed plies of fibrous cellulosic material. The contact pressure, temperature, strength and modulus of the materials and/or other factors may influence how the cellulosic material is apparently deformed and momentarily transformed into what might be characterized as a viscous state. If factors such as, for example, surface polarity, surface morphology, moisture, viscosity, crystallinity (if any) are appropriate, crimp-bonds are formed. Crimp-bonding is generally attributed to van der Waals' forces as well as mechanical bonding (e.g., entangled, interlocked and smashed and/or crushed fibers) which may be created when relatively high pressure loads are applied. A small portion of the crimp-bonds may be attributed to hydrogen bonding (e.g. "paper bonding") which may be induced by the combination of high pressure loads and certain moisture levels in the fibrous cellulosic plies.

As used herein, the term "fibrous cellulosic material" refers to a nonwoven web of cellulosic fibers that has a structure of individual fibers which are interlaid, but not in an identifiable repeating manner. Such webs have been, in the past, formed by a variety of nonwoven manufacturing processes known to those skilled in the art such as, for example, air-forming, wet-forming and/or papermaking processes. Exemplary fibrous cellulosic materials include papers, tissues and the like. Such materials can be treated to impart desired properties utilizing processes such as, for example, calendering, creping, hydraulic needling, hydraulic entangling and the like. Generally speaking, the cellulosic fibrous material may be prepared from cellulose fibers from natural sources such as woody and non-woody plants. Woody plants include, for example, deciduous and coniferous trees. Non-woody plants include, for example, cotton, flax, esparto grass, milkweed, straw, jute, hemp, and bagasse. The cellulose fibers may be modified by various treatments such as, for example, thermal, chemical and/or mechanical treatments. It is contemplated that reconstituted and/or synthetic cellulose fibers may be used and/or blended with other cellulose fibers of the fibrous cellulosic material.

As used herein, the term "area of localized surface contact" refers to a discrete zone on a material (e.g., plies of a fibrous cellulosic material) that is impressed by an individual protuberance or knurl on a rotating crimp element having protuberances or knurls. Generally speaking, the material is positioned between the rotating crimp element and a rotating smooth non-resilient anvil roll (e.g., a smooth, hardened metal anvil roll). Contact is made while a pressure load is placed against the crimp element and anvil element to concentrate the pressure load at the discrete zone of contact.

As used herein, the term "crimp-bonding at an overall distribution of spaced-apart locations" refers to placement of crimp-bonds at discontinuous discrete locations over an entire surface of a laminate material. For example, an overall distribution of crimp-bonds may be described as crimp-bonds scattered across the surface of a laminate instead of crimp-bonds placed in a linear configuration along the edges of a laminate. An overall crimp-bonded fibrous cellulosic laminate is believed to provide better ply attachment than conventional edge crimp-bonded fibrous cellulosic laminates.

As used herein, the term "basis weight" refers to the weight of a material per specified unit of surface area. This measure is usually associated with relatively thin, flat, sheet-like materials such as, for example, fabrics, films, papers, webs and the like. Basis weights of the materials discussed herein were determined essentially in accordance with Method 5041 of Federal Test Method Standard No. 191A. Basis weight is expressed in units of weight per unit of area (e.g., grams per square meter or ounces per square yard).

As used herein, the term "machine direction" refers to the planar dimension of a fibrous web (e.g., fibrous cellulosic web) which is in the direction of travel of the forming surface onto which fibers are deposited during formation of the web.

As used herein, the term "cross-machine direction" refers to the planar dimension of a fibrous web which is in the direction that is perpendicular to the machine direction defined above.

As used herein, the term "outer surface" refers to the face of a layer or ply of a multi-ply material which is oriented toward or actually composes the exterior portion of the multi-ply material.

As used herein, the term "inner surface" refers to a layer which is not an outer surface.

SUMMARY OF THE INVENTION

The problems described above are addressed by the process of the present invention which is directed to a process of producing an absorbent fibrous cellulosic laminate including the steps of: 1) providing at least two superposed plies of a fibrous cellulosic material; 2) passing the superposed plies through a crimp roll arrangement including a rotating crimp element and a rotating anvil element, the crimp element having protruding members configured in a discontinuous pattern aligned on an axis that is parallel to the cross-machine direction providing a substantially continuous uniform area of localized surface contact between the rotating elements across the width of the plies; and 3) applying a pressure load against the rotating elements sufficient to crimp-bond the fibrous cellulosic material plies into a laminate, Desirably, the process should produce a laminate having a machine direction adhesion strength of at least about 18 grams per 2 inches of width.

According to the process of the present invention, the crimp element may be a single pattern roll or a series of pattern rolls. The anvil element may be a smooth anvil roll. Desirably, the pattern roll(s) and the anvil roll are hardened-metal rolls. The rotating elements have a substantially continuous uniform area of localized surface contact which produces a bonded surface area on the fibrous cellulosic materials that may range from about 1 to about 15 percent of the total surface area of the laminate. For example, the bond surface area may be from about 2 to about 7 percent of the total surface area of the laminate. Desirably, the bond surface area may be about 3 percent of the total surface area of the laminate.

According to one aspect of the process a pressure load is applied against the rotating elements so that the load on the plies of fibrous cellulosic material between the elements is greater than about 900 pounds per linear inch across the areas of localized surface contact. For example, the pressure load may be greater than about 1500 pounds per linear inch across the areas of localized surface contact. As a further example, the pressure load may be greater than about 2000 pounds per linear inch across the areas of localized surface contact.

In another aspect of the process, the plies of fibrous cellulosic material may have a moisture content of at least about 2 percent, by weight. For example, at least one ply of fibrous cellulosic material may have a moisture content of from about 2.5 to about 9 percent, by weight.

The present invention encompasses an absorbent crimp-bonded fibrous cellulosic laminate material composed of at least two plies of a fibrous cellulosic material joined by crimp-bonding at an overall distribution of discontinuous spaced-apart locations arranged to provide a substantially continuous uniform bond surface area across the width of the plies. The bond surface area may range from about 1 to about 15 percent of the total surface area of the laminate. For example, the bond surface area may be from about 2 to about 7 percent of the total surface area of the laminate. Desirably, the bond surface area may be about 3 percent of the total surface area of the laminate.

Desirably, crimp-bonding between the fibrous cellulosic material plies may provide a machine direction adhesion strength of at least about 18 grams per 2 inches of width. For example, the crimp-bonding between the individual plies of fibrous cellulosic material may produce a machine direction adhesion strength of at least about 20 grams per 2 inches of width. As a further example, the crimp-bonding between the individual plies of fibrous cellulosic material may produce a machine direction adhesion strength of at least about 22 grams per 2 inches of width.

According to the invention, individual bond locations on the laminate material may have a surface area ranging from about 0.1 to about 0.3 cm². Desirably, each bond may have a surface area of about 0.2 cm².

The individual plies of fibrous cellulosic material in the laminate may have basis weights ranging from about 4 to about 34 grams per square meter. For example, the individual plies of fibrous cellulosic material may have a basis weight of about 7 grams per square meter. The total basis weight of the laminate may range from about 8 to about 68 grams per square meter. For example, total basis weight may be about 14 grams per square meter. In one embodiment of the invention, plies having different basis weights may be joined into an crimp-bonded laminate.

According to one aspect of the present invention, the laminate material may have a thickness that is at least 2 percent greater than that of an identical un-bonded laminate or edge crimp-bonded laminate. For example, the laminate material may have a thickness ranging from about 2 to about 3 percent greater than an identical un-bonded laminate or edge crimp-bonded laminate.

The fibrous cellulosic material may be any fibrous cellulosic material suitable for crimp-bonding operations. Desirably, the fibrous cellulosic material is a cellulosic tissue. A crimp-bonded laminate material may be composed of more than two plies of a fibrous cellulosic material. For example, three plies, four plies, or more may be used. These plies may be superposed or cross-lapped. Individual plies may also have multi-layer construction such as, for example, a layered construction obtained by using a serial headbox arrangement in a wet-forming process.

The present invention also encompasses an apparatus for crimp-bonding multiple superposed plies of a fibrous cellulosic material. The apparatus includes 1) a rotating hardened-metal crimp element; 2) a rotating smooth hardened-metal anvil element; 3) protruding members configured on the surface of the crimp element in a discontinuous pattern aligned on an axis that is parallel to the cross-machine direction providing a substantially continuous uniform area of localized surface contact between the rotating elements across the width of the plies; and 4) means to apply pressure against the rotating elements so that the pressure load on multiple superposed plies of a fibrous cellulosic material at each area of localized surface contact is sufficient to crimp-bond the plies into a laminate having a machine direction adhesion strength of at least about 18 grams per 2 inches of width. The crimp element may be a single hardened-metal pattern roll or a series of hardened-metal pattern rolls. The anvil element may be a smooth, hardened-metal anvil roll.

DETAILED DESCRIPTION OF THE INVENTION

Figure 1:
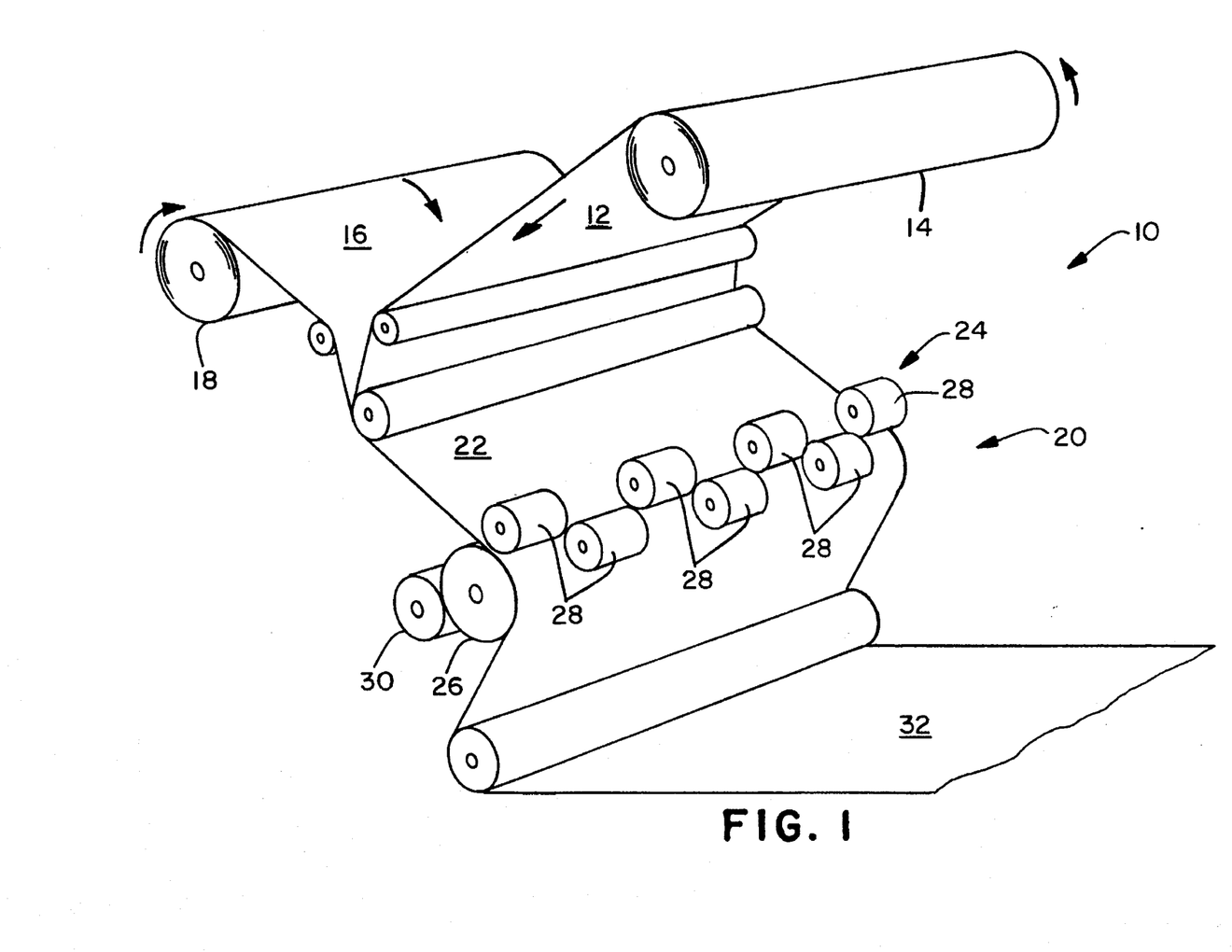
FIG. 1 is an illustration of an exemplary process and apparatus for making an absorbent overall crimp-bonded fibrous cellulosic laminate.

Referring to the drawing and in particular to FIG. 1, there is shown at 10 an illustration of an exemplary process and apparatus of the present invention for making an overall crimp-bonded fibrous cellulosic laminate.

According to the present invention, a first ply of a fibrous cellulosic material 12 is unwound from a supply roll 14 and travels in the direction indicated by the arrow associated therewith as the supply roll 14 rotates in the direction of the arrows associated therewith. A second ply of a fibrous cellulosic material 16 is unwound from a supply roll 18 and travels in the direction indicated by the arrow associated therewith as the supply roll 18 rotates in the direction of the arrows associated therewith. The plies 12 and 16 are superposed (and/or cross-lapped) before being introduced directly into the crimp roll arrangement 20. Alternatively, the plies of fibrous cellulosic material 12 and 16 may be wound together on a single supply roll (not shown) in superposed configuration. It is contemplated that more than two plies may be used in the process of the present invention.

The plies of fibrous cellulosic material 12 and 16 may be formed by one or more paper-making processes, dried to an acceptable moisture content, and passed directly into the crimp roll arrangement 20 without first being stored on supply rolls 14 and 18.

The plies 12 and 16 may be passed through a pretreatment station (not shown) to modify a surface (or surfaces) of the fibrous cellulosic material. For example, the plies may be calendered or pressed in order to achieve desired physical and/or textural characteristics. Additionally, at least a portion of a surface (or surfaces) may be modified by various known surface modification techniques. Exemplary surface modification techniques include, for example, oxidation, ion bombardment, plasma treatments, steam treatments, heat treatments, and/or corona discharge treatments.

The superposed plies 22 pass through the nip of a crimp roll arrangement 20 including a rotating crimp element 24 and a rotating anvil element 26. According to the invention, the rotating crimp element 24 may be composed of multiple rotating crimp rolls 28 arranged in banks contacting one or more rotating anvil elements 26 across the width of the superposed plies. For example, the crimp element 24 may be a series of hardened-metal pattern rolls. The anvil element 26 may be a smooth, hardened-metal anvil roll.

FIG. 1 depicts an exemplary crimp roll arrangement 20 containing a crimp element 24 composed of a first bank and a second bank of crimp rolls 28. The banks of crimp rolls 28 are offset but arranged in parallel so that the full width (or partial width) of the superposed cellulosic material plies 22 are treated. The crimp roll arrangement 20 also contains a smooth, hardened metal anvil roll 26 and a drive roll 30. According to the invention, the crimp element 24 may be a single hardened-metal pattern roll (not shown). As the superposed plies 22 pass through the crimp roll arrangement 20, they pass between the crimp element 24 and the anvil element 26 and are crimp-bonded into a laminate 32. The laminate may be slit to different widths, wound up on a roll and/or subjected to post-treatments and the like. Desirably, very wide rolls having commercially acceptable diameters may be cut to desired widths.

Figure 2:
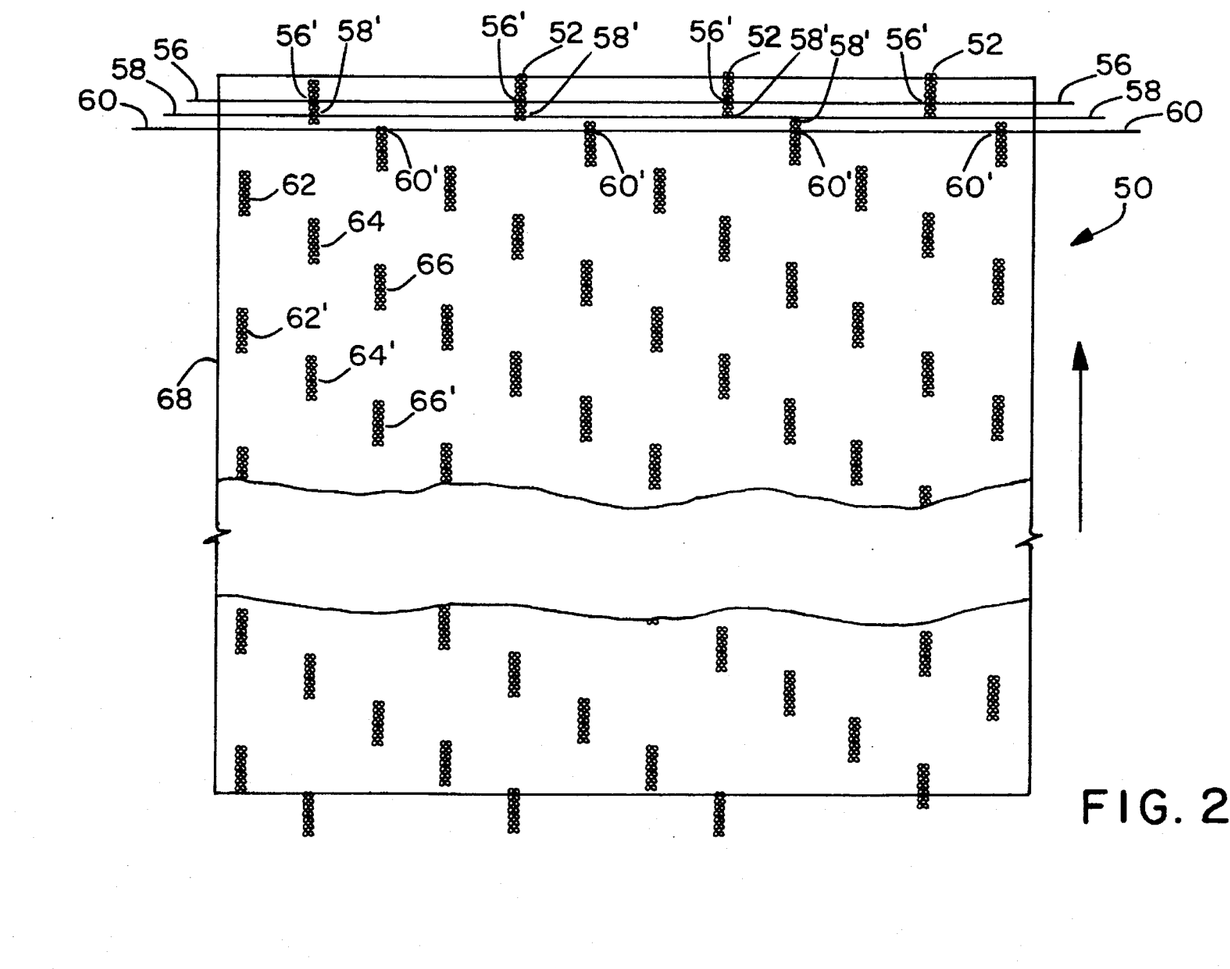
FIG. 2 is an illustration of a flat projection of the surface of an exemplary crimp roll.

Referring now to FIG. 2 of the drawings, there is shown (not necessarily to scale) a flat projection 50 of the surface of a crimp roll as it would appear as if it was unrolled from the roll. The flat projection 50 has protruding members 52 configured in a discontinuous pattern aligned on an axis that is parallel to the cross-machine direction of the cellulosic laminate being processed. For purposes of this illustration, some of the protruding members 52 are shown to extend beyond or off the flat projection 50.

Figure 3A:
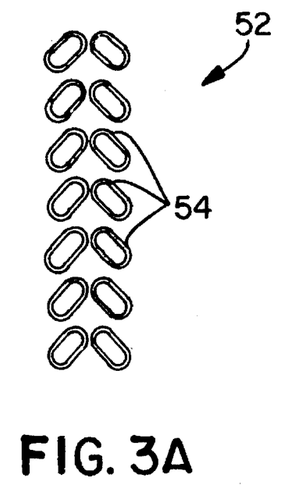
FIGS. 3A, 3B and 3C are illustrations of an exemplary individual protruding member on crimp roll.
Figure 3B:
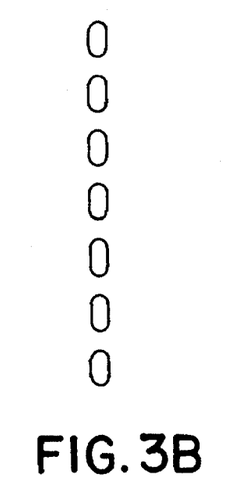
Figure 3C:
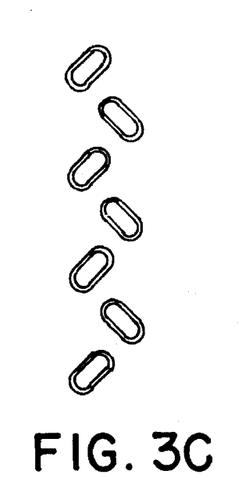
Figure 3D:
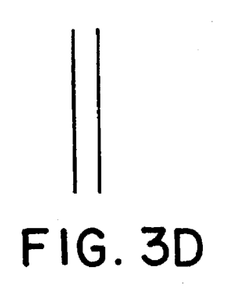
FIGS. 3D, 3E and 3F are illustrations of exemplary overall shapes of protruding members.
Figure 3E:
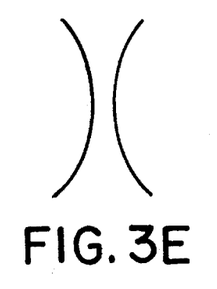
Figure 3F:
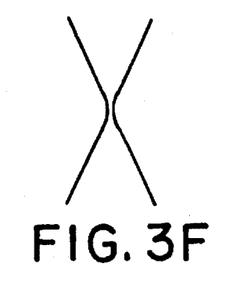
Figure 3G:
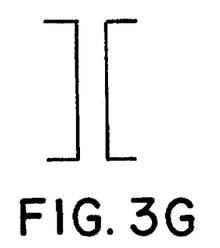
FIG. 3G is an illustration of an unsatisfactory exemplary overall shape of a protruding member.

A top view of an exemplary protruding member 52 is shown in FIG. 3A of the drawings (not necessarily to scale). An individual protruding member 52 is made up of identical elements 54. The elements are arranged so that the surface area of an individual protruding member 52 in contact with the fibrous cellulosic laminate remains substantially constant as the crimp roll rotates. A few of the many possible arrangements of elements 54 are also depicted in FIG. 3B and FIG. 3C. As can be seen from these examples, the longest dimension of a protruding member will be aligned in the general direction of rotation of the crimp roll. For example, the protruding members may have overall shapes approximately corresponding to FIG. 3D, FIG. 3E or FIG. 3F. A shape such as that shown in, for example, FIG. 3G does not appear to provide a substantially continuous uniform surface area of contact between an individual protruding member 52 and the fibrous cellulosic laminate as the crimp roll rotates.

Generally speaking, an individual protruding member 52 has a total surface area (which comes in contact with the cellulosic laminate) of about 0.1 to about 0.3 $cm^2$. Desirably, an individual protruding member 52 has a total surface area of about 0.2 $cm^2$. This surface corresponds closely to the surface area of each bond location on the laminate material. Each bond location on the laminate material may have a surface area ranging from about 0.1 to about 0.3 $cm^2$. Desirably, each bond may have a surface area of about 0.2 $cm^2$.

Referring again to FIG. 2 of the drawings, it can be seen that the protruding members 52 are configured in a discontinuous pattern. An evident feature of this pattern is that the protruding members are aligned parallel to the machine direction of the superposed plies of fibrous cellulosic material 22 being processed. A less evident but more important feature can be observed by examining the pattern in the axis that is parallel to the cross-machine direction of the superposed plies of fibrous cellulosic material. It can be seen that the protruding members 52 on the crimp element are configured to provide a substantially continuous uniform area of localized surface contact on the superposed plies of fibrous cellulosic material 22 between the crimp element and the anvil element.

For example, a line 56 drawn across the crimp element parallel to the cross-machine direction of the superposed plies of fibrous cellulosic material 22 intersects protruding members 52 at four locations 56' which would appear as bond points on the fibrous cellulosic laminate when the crimp element and anvil element contacted the superposed plies under sufficient pressure. The line 56 is drawn so that it is parallel to the cross-machine direction of the superposed plies of fibrous cellulosic material 22 being processed. The arrow which is generally perpendicular to this line indicates the direction of rotation as well as the machine direction of the superposed plies of fibrous cellulosic material. A second line 58 is drawn across the crimp element a small distance from and parallel to the first line 56. The second line 58 intersects protruding members 52 at four locations 58' which would appear as bond points on the cellulosic laminate. A third line 60 is drawn across the crimp element a small distance from and parallel to the first line 58. The third line 60 intersects protruding members 52 at four locations 60' which would appear as bond points on the cellulosic laminate. Even if the spacing between the lines is reduced, the lines intersect protruding members 52 at the same number of locations. Thus, a wide crimp roll may be designed to contact the anvil roll at a large, but constant, number of locations. That is, the summation of the interrupted lines of contact across the width of the roll as the roll rotates will remain substantially uniform.

As discussed above, the surface area of an individual protruding member in contact with the anvil element is configured to remain substantially uniform as both elements rotate. Since the same number of protruding members are in contact with the anvil element as both the crimp element and anvil element rotate, the areas of localized surface contact between the crimp element and the anvil element (i.e., of a particular set of crimp element and anvil element) should be substantially and continuously uniform. Of course, the total area of contact may be varied by uniformly changing the distribution density and/or surface areas of individual protruding members on a crimp element. However, the area of contact should remain uniform as long as the individual protuberances are properly positioned.

To illustrate this point further, individual protruding members 62, 64 and 66 are identified in FIG. 2. One protruding member 62 is adjacent an outer edge 68 of the crimp roll. Another protruding member 64 is positioned slightly further from the outer edge 68 and slightly offset from the outermost protruding member 62. Yet another protruding member 66 is positioned even further from the outer edge 68 and slightly offset from the next outermost protruding member 64. A similar configuration of individual protruding members 62', 64' and 66' are also identified in FIG. 2.

Figure 4:
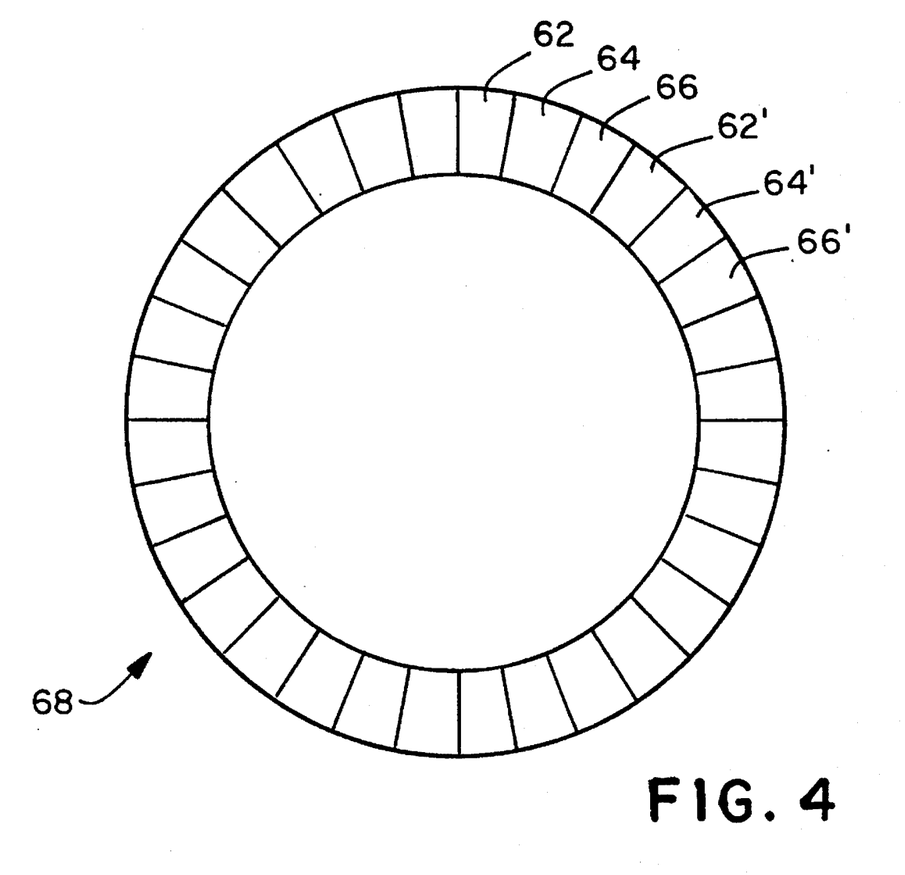
FIG. 4 is a cross-sectional view of an exemplary crimp roll.

Referring now to FIG. 4 of the drawings, there is shown an illustration of a cross-sectional view of the crimp roll depicted as a flat projection in FIG. 2. When viewed from the outer edge 68, the crimp roll presents an apparently continuous placement of protruding members. Namely, the protruding member 62 adjacent the outer edge 68 of the crimp roll is in plain view. A protruding member 64 positioned slightly further from the outer edge 68 and slightly offset from the outermost protruding member 62 is also substantially in plain view. Yet another protruding member 66 positioned even further from the outer edge 68 and slightly offset from the next outermost protruding member 64 is also in substantially plain view. This pattern repeats itself with another set of individual protruding members 62', 64' and 66'.

Figure 5:
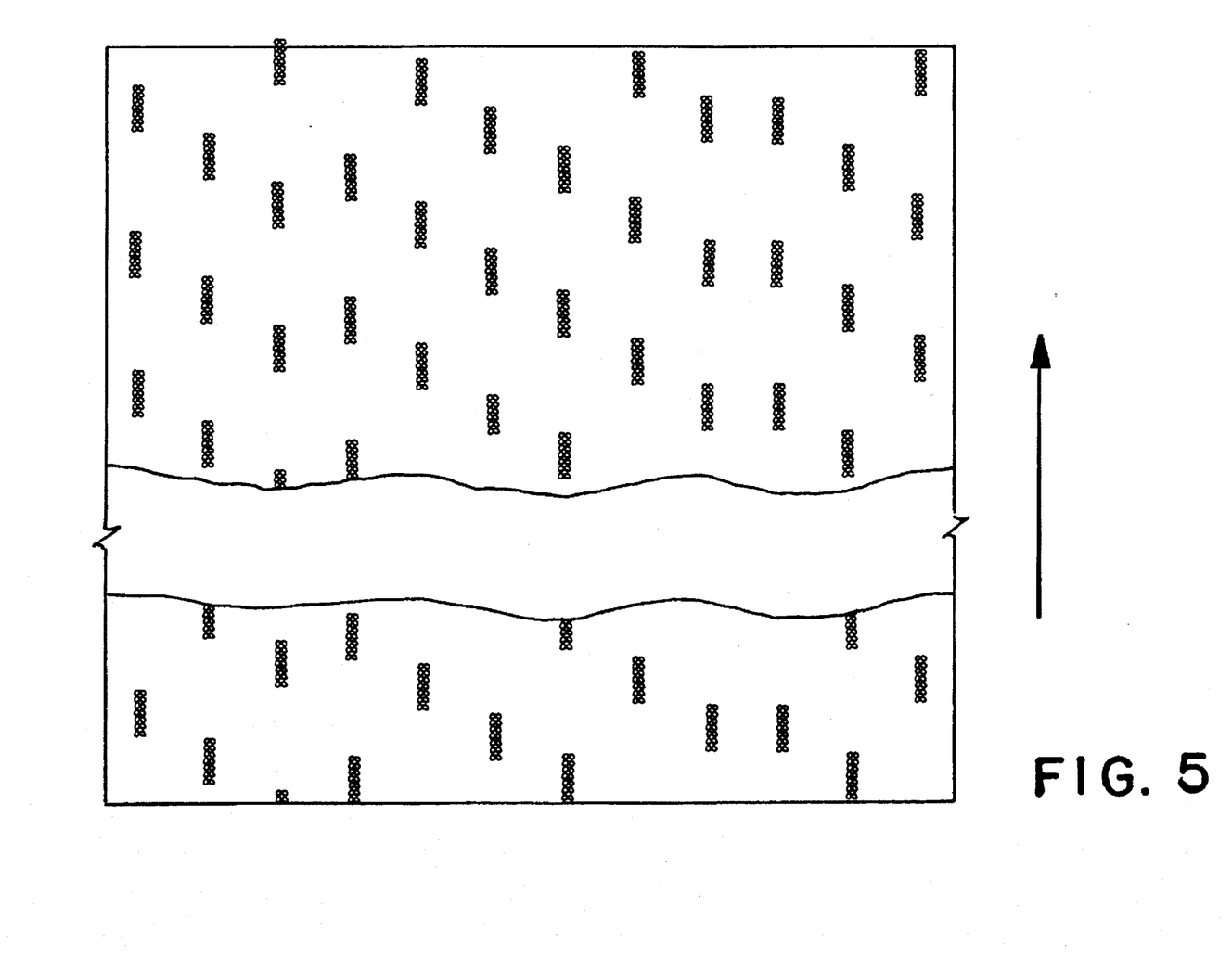
FIG. 5 is an illustration of an exemplary pattern of crimp-bond points on a cellulosic laminate.

The pattern of protruding members 52 shown in FIG. 2 appears as a generally ordered arrangement on an individual crimp roll. The protruding members 52 may be configured to suggest a more random distribution and still provide a substantially continuous uniform area of localized surface contact between the crimp element and the anvil element. For example, FIG. 5 is an illustration of a flat projection of the surface of an exemplary crimp roll (of a crimp element) depicting an offset pattern. The arrow in FIG. 5 indicates the direction of rotation. The dimension that is generally perpendicular to this arrow is parallel to the cross-machine direction of the cellulosic laminate being processed.

It may be desirable to ensure that the pattern of protruding members is balanced across the width of the crimp roll. That is, it may be desirable to avoid patterns which may concentrate protruding members on one side of a crimp roll (even if the pattern provides a substantially continuous uniform area of localized surface contact between the crimp element and the anvil element) because such uneven or asymmetric patterns may produce instability or rocking of the crimp roll during high-speed operation.

Figure 6:
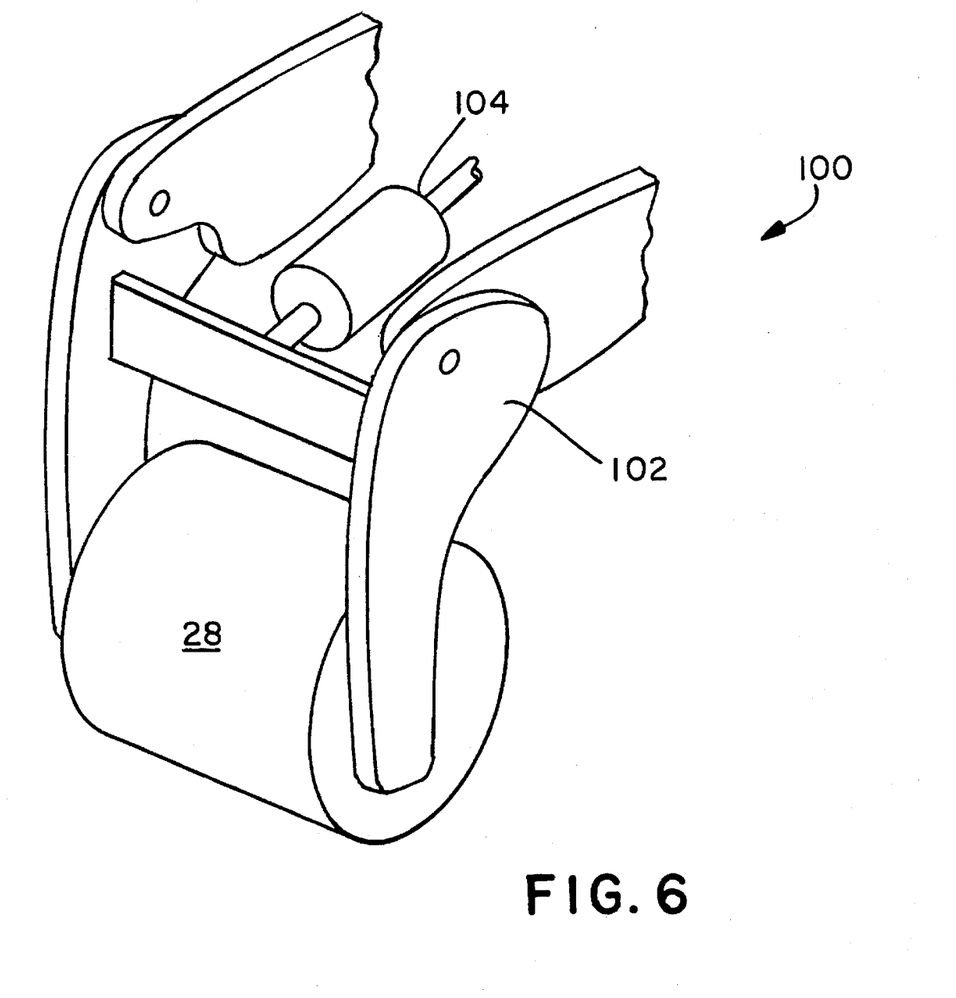
FIG. 6 is an illustration of an exemplary crimp roll assembly.

Referring to FIG. 6 of the drawings, there is shown an exemplary crimp roll assembly 100. The crimp roll assembly 100 includes a crimp roll 28 installed in a crimp roll holder 102. The crimp roll 28 may have a width ranging from about 4 to about 135 inches or more. For example, the crimp roll may be from about 4.5 to about 60 inches wide. As a further example, the crimp roll may be about 4.5 to about 12 inches wide. Diameter of the crimp roll may range from about 4 to about 9 inches. For example, diameter of the crimp roll may range from about 6 to about 7 inches. It is generally desirable for both the crimp roll and the anvil roll to have relatively small diameters. Combinations of relatively small diameter rolls (i.e., crimp roll and anvil roll combinations) present less total contact surface area and generally concentrate a given pressure load more effectively than combinations of relatively large diameter rolls.

Pressure generating means 104 (e.g., hydraulic cylinders, air cylinders, air loading means, weights, springs, gear systems, screw systems or the like) are used to apply relatively high pressure loads against the roll holder 102 which is transferred to the crimp roll 28. This assembly 100 is mounted on a support member (not shown) which is rigid and has sufficient strength to cope with pressure loads between the crimp roll and anvil roll that are normally greater than 300 pounds of reactive force. These loads can also be expressed as greater than about 900 pounds per linear inch across the areas of localized surface contact. For example, these loads may be greater than about 1500 pounds per linear inch across the areas of localized surface contact. As a further example, these loads may be greater than 2000 pounds per linear inch across the areas of localized surface contact. The substantially continuous uniform area of localized surface contact described above enables a relatively large pressure load to be applied against the rotating crimp and anvil elements without the destructive vibration or "chattering" encountered in many hard pattern roll/hard anvil processes.

The process of the present invention can be configured to provide a cross-machine direction, registered or non-registered pattern so that wide rolls of laminate may be slit or cut into products that do not have a misaligned bond pattern. Ply attachment may be much greater than that obtained with conventional edge crimp-bonding processes and without substantial change to the overall thickness of the sheet. In addition, the base sheet characteristics outside the crimped area (i.e., from about 85 to about 99 percent of the surface area of the sheet) remain essentially unchanged. Another advantage of the process of the present invention is that it can accommodate various roll widths without adjustments to the crimp elements. Also, different crimp elements (i.e., differently patterned crimp rolls) could be run against the same anvil.

The present invention encompasses a crimp-bonded fibrous cellulosic laminate. This laminate is composed of 1) a first ply of a fibrous cellulosic material, and 2) a second ply of a fibrous cellulosic material joined to the first ply by crimp-bonding at an overall distribution of spaced-apart locations arranged to provide a continuously uniform bond surface area across the width of the plies.

Generally speaking, the crimp-bonding between the fibrous cellulosic material plies should provide a machine direction adhesion strength of at least about 18 grams per 2 inches of width. For example, the crimp-bonding between the individual plies of fibrous cellulosic material should produce a machine direction adhesion strength of at least about 20 grams per 2 inches of width. Desirably, the crimp-bonding between the individual plies of fibrous cellulosic material will provide a machine direction adhesion strength of at least about 22 grams per 2 inches of width.

Adhesion strength measurements for an edge crimped-bonded laminate and an overall crimp-bonded laminate show that the overall crimped-bonded laminate has bonds which provides an average ply attachment (i.e., mean adhesion strength) in the machine direction that may be about 10 to about 40 percent greater than a conventional edge crimp-bonded laminate. For example, the mean adhesion strength (machine direction) may be about 20 to about 35 percent greater than a conventional edge crimped-bonded laminate. Improvement to machine direction ply attachment (i.e., adhesion strength) is important because most multiple-ply cellulosic laminates in roll form are wound along the laminate's machine direction. Thus, unwinding or dispensing the roll may generate peeling forces along the machine direction. In addition, greater ply attachment could allow for errors in crimping such as, for example, skipped crimps, incorrect number of crimps, punched-out crimps and the like.

One characteristic of the laminate is that the surface area of the crimp-bond locations generally ranges from about 1 to about 15 percent of the total surface area of the laminate. The bond surface area may be from about 2 to about 15 percent of the total surface area of the laminate. For example, the bond surface area may be about 12 percent of the total surface area of the laminate. It may be desirable to have relatively low levels of bond surface area, primarily to enhance the quilted or pillowed appearance of the laminate. The material between the bond locations tends to separate producing a soft, cushioned appearance. Each bond location on the laminate material may have a surface area ranging from about 0.1 to about 0.3 cm². Desirably, each bond may have a surface area of about 0.2 cm².

The fibrous cellulosic material may be any material which is suitable for conventional linear edge crimp-bonding operations. Generally speaking, the fibrous cellulosic material may be a cellulosic tissue.

The individual plies of fibrous cellulosic material in the laminate may have basis weights ranging from about 4 to about 34 grams per square meter. The total basis weight of the laminate may range from about 8 to about 68 grams per square meter. Plies having different basis weights may be joined into an absorbent crimp-bonded laminate. The absorbent crimp-bonded laminate may be composed of more than two plies of a fibrous cellulosic material. For example, three plies, four plies, or more may be used. Individual plies may also have multi-layer construction.

Generally speaking, the plies of fibrous cellulosic material may have a moisture content of at least about 2 percent, by weight. For example, at least one ply of fibrous cellulosic material may have a moisture content of from about 2.5 to about 9 percent, by weight. Although the inventors should not be held to a particular theory of operation, it is thought that the combination of moisture in the fibrous cellulosic material and the pressure of the crimp process may produce hydrogen bonding (e.g., "paper" bonding) between the plies. It is contemplated that the moisture content of the cellulosic material may be modified to take advantage of this possible source of added ply attachment.

Referring now to FIGS. 7–10, these figures are microphotographs of cross-sectioned fibrous cellulosic laminates. Specimens were placed in liquid nitrogen and then cut through at the bond points. Cross-sections were plated and then photographed utilizing a Cambridge 5-200 scanning electron microscope available from Leica, Inc. of Deerfield, Ill. Thickness of the sample cross-sections at the bond points was measured with the electronic cursor of the scanning electron microscope.

Figure 7:
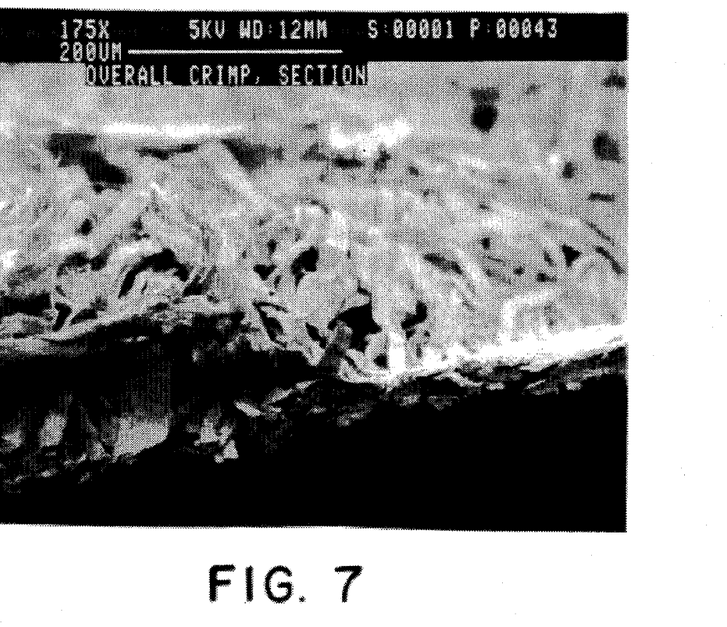
FIG. 7 is a microphotograph of an exemplary overall crimp-bonded fibrous cellulosic laminate.
Figure 8:
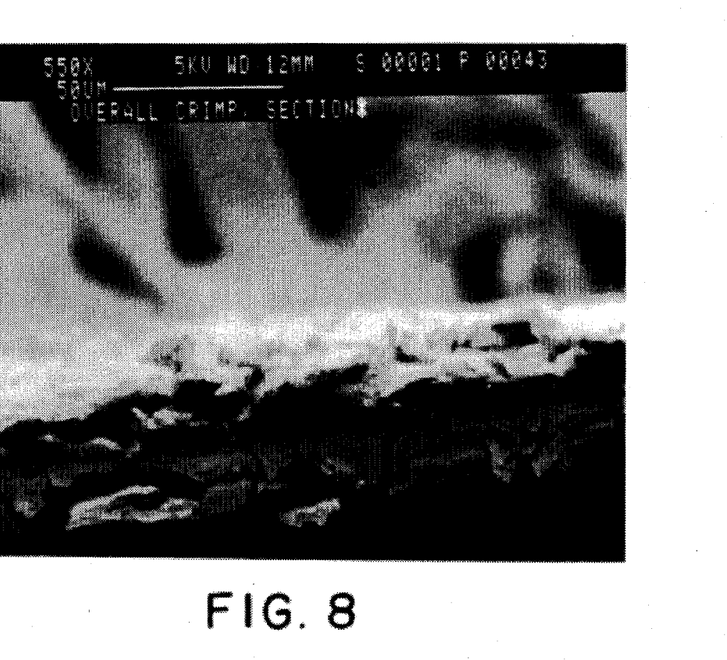
FIG. 8 is a microphotograph of an exemplary overall crimp-bonded fibrous cellulosic laminate.

FIG. 7 is a 175× (linear magnification) photomicrograph of a cross-section of an exemplary overall crimp-bonded fibrous cellulosic laminate (i.e., bonding at an overall distribution of spaced-apart locations arranged to provide a continuously uniform bond surface area across the width of the plies). FIG. 8 is a 550× (linear magnification) photomicrograph of a cross-section of an exemplary overall crimp-bonded fibrous cellulosic laminate.

Figure 9:
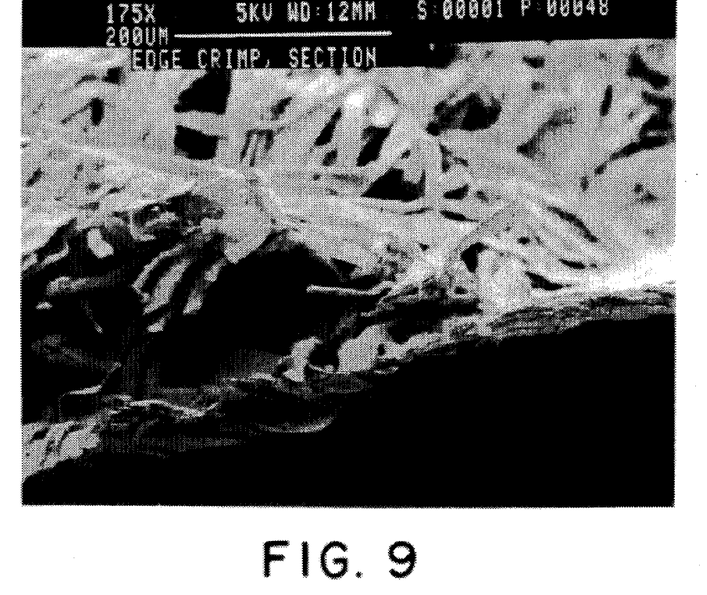
FIG. 9 is a microphotograph of a conventional edge-crimped fibrous cellulosic laminate.
Figure 10:
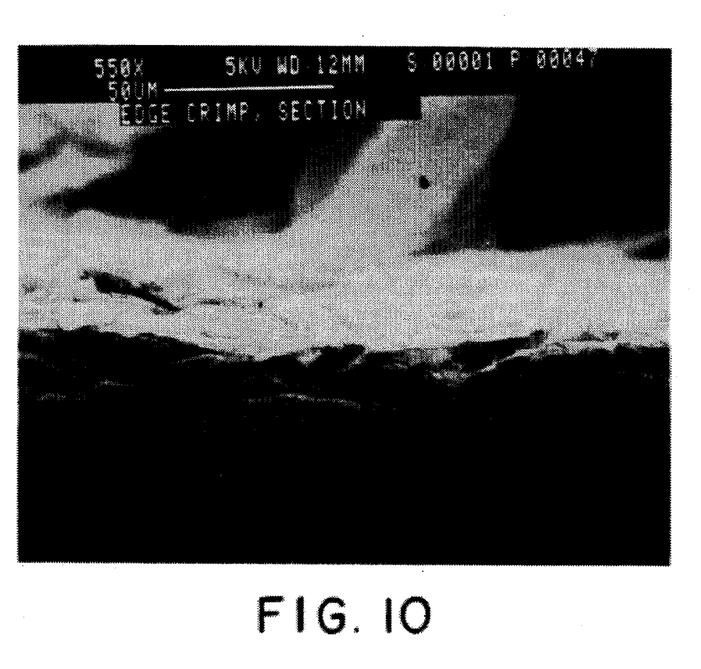
FIG. 10 is a microphotograph of a conventional edge-crimped fibrous cellulosic laminate.

FIG. 9 is a 175× (linear magnification) photomicrograph of a cross-section of a conventional edge crimp-bonded fibrous cellulosic laminate. FIG. 10 is a 550× (linear magnification) photomicrograph of a cross-section of a conventional edge crimp-bonded fibrous cellulosic laminate. As can be seen from a comparison of FIGS. 7 and 8 with FIGS. 9 and 10, the overall crimp-bonded laminate appears to have a thicker bond width and more unattached fibers than the conventional edge crimp-bonded laminate. The conventional edge crimp-bonded laminate has a bond width of about 12–15 microns while the overall crimp-bonded laminate has a bond width of about 31 microns.

The overall distribution of crimp-bonds imparts a quilted or "pillow-like" appearance to the overall crimp-bonded laminate. Thickness measurements of the edge crimp-bonded laminate and the overall crimp-bonded laminate show that the overall crimp-bonded laminate may be from about 1 to about 5 percent thicker than the edge crimp-bonded laminate. For example, the thickness may be about 2 to 3 percent greater than the edge crimp-bonded laminate. Thickness measurements show that a stack of 10 sheets of the overall crimp-bonded laminate may be from about 3 to about 5 percent thicker than an identical stack of the edge crimp-bonded laminate. For example, the thickness may be about 3 to 4 percent greater than an identical stack of the edge crimp-bonded laminate.

EXAMPLES

Examples were prepared generally in accordance with the process described above. A first ply of a fibrous cellulosic tissue was unwound from a supply roll. A second ply of fibrous cellulosic tissue was unwound from a second supply roll. Each ply had a basis weight of about seven (7) grams per square meter and a width of about nine (9) inches. The plies were superposed and passed through the nip of a crimp roll arrangement. The crimp roll arrangement included hardened-steel crimp rolls and a smooth, hardened-steel anvil roll. Each crimp roll measured about 9 inches in width and about 6 inches in diameter.

The crimp rolls (i.e., pattern rolls) had protruding members configured in a discontinuous pattern aligned on an axis parallel to the cross-machine direction of the tissue plies. The pattern was designed to provide a substantially continuous uniform area of localized surface contact between the crimp element and the anvil element generally as shown in FIG. 2 of the drawings (not necessarily to scale).

Each protruding member was made up of identical elements generally as shown in FIG. 3A of the drawings (not necessarily to scale). The elements were arranged so that the surface area of an individual protruding member in contact with the tissue cellulosic laminate remained constant as the crimp element rotates. Accordingly, the longest dimension of a protruding member was generally aligned to the direction of rotation of the crimp element. Each protruding member had a total surface area which comes in contact with the tissue plies of about 0.2 cm².

Conventional air-pressure loading means were used to apply a pressure load against the crimp roll of about 300 pounds of reactive force. A total load was calculated from the pressure load and the combined weights of the crimp roll and crimp roll mount. The total pressure load was calculated to be about 886 pounds per linear inch of contact across the areas of localized surface contact (i.e., width of the plies). After crimping, the laminate was wound onto a roll and cut into rolls having a width of about 4.5 inches.

The adhesion strength measurements for the crimp-bonded laminate samples generally conformed to ASTM Standard Test D 2724.13 and to Method 5951, Federal Test Methods Standard No. 191A, with the following changes: 1) the specimen size was 2 inches by 6 inches (6 inches in the machine direction); 2) the gauge length was set at one inch; and 3) the value of the peak load alone was interpreted as the bond strength of the specimen. The bond strength of the sample unit was calculated as the average peak load of all the specimens tested. The adhesion strength between plies of control samples (i.e., edge-crimped-bonded laminates) was measured and reported for comparison. All adhesion strength and tensile strength testing was conducted using an Instron Model 1122 Universal Test Instrument available from Instron Corporation, Canton, Mass.

The adhesion strength (i.e., peak load) for overall crimp-bonded tissue laminates produced as described above and for conventionally produced edge crimp-bonded tissue laminates are reported in Tables 1–4. The conventionally produced edge crimp-bonded tissue laminates were made from the same 7 grams per square meter plies used for the overall crimp-bonded tissue.

As can be seen from Tables 1 and 2, the overall crimp-bonded tissue laminate has a machine direction adhesion strength (i.e., peak load) that is about 32.5 percent greater than the conventional edge crimp-bonded tissue laminate. This difference is significant at the 95 percent confidence level. As can be seen from Tables 3 and 4, no significant differences are noticed in the cross-machine direction adhesion strength.

The thickness (i.e., bulk) of the samples was measured with a Model 49-70 thickness tester available from TMI (Testing Machines Incorporated) of Amityville, N.Y. The thickness tester was equipped with a 2-inch diameter circular foot and measurements were taken at an applied pressure of about 0.2 pounds per square inch (psi). Results of the thickness measurements are reported in Table 5.

Thickness measurements of the edge crimp-bonded laminate and the overall crimp-bonded laminate show that the overall crimp-bonded laminate is about 2.4 percent thicker than the edge crimp-bonded laminate. Thickness measurements show that a stack of 10 sheets of the overall crimp-bonded laminate is about 3.2 percent thicker than an identical stack of the edge crimp-bonded laminate.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

TABLE 1

OVERALL CRIMP - MACHINE DIRECTION

| Specimen | Peak Load grams/2" width |
|---|---|
| 1 | 18.823 |
| 2 | 24.200 |
| 3 | 15.237 |
| 4 | 19.719 |
| 5 | 20.615 |
| Mean | 19.719 |
| Min | 15.237 |
| Max | 24.200 |
| StdDev | 3.232 |
| Median | 19.719 |

TABLE 2

EDGE CRIMP - MACHINE DIRECTION

| Specimen | Peak Load grams/2" width |
|---|---|
| 1 | 17.926 |
| 2 | 14.789 |
| 3 | 11.204 |
| 4 | 14.789 |
| 5 | 15.685 |
| Mean | 14.879 |
| Min | 11.204 |
| Max | 17.926 |
| StdDev | 2.422 |
| Median | 14.789 |

TABLE 3

OVERALL CRIMP - CROSS-MACHINE DIRECTION

| Specimen | Peak Load grams/2" width |
|---|---|
| 1 | 26.889 |
| 2 | 36.749 |
| 3 | 24.200 |
| 4 | 18.823 |
| 5 | 29.578 |
| Mean | 27.248 |
| Min | 18.823 |
| Max | 36.749 |
| StdDev | 6.635 |
| Median | 26.889 |

TABLE 4

EDGE CRIMP - CROSS-MACHINE DIRECTION

| Specimen | Peak Load grams/2" width |
|---|---|
| 1 | 38.541 |
| 2 | 19.719 |
| 3 | 27.786 |
| 4 | 43.023 |
| 5 | 36.749 |
| Mean | 33.164 |
| Min | 19.719 |
| Max | 43.023 |
| StdDev | 9.336 |
| Median | 36.749 |

TABLE 5

| Sample ID | THICKNESS (inches) | |
| --- | --- | --- |
| | Mean | StdDev |
| Two-ply tissue - 10 sheets W/Edge Crimping | 0.07471 | 0.00185 |
| Two-ply tissue - 1 sheet W/Edge Crimping | 0.00841 | 0.00110 |
| Two-ply tissue - 10 sheets Overall Crimped | 0.07713 | 0.00226 |
| Two ply tissue - 1 sheet Overall Crimped | 0.00860 | 0.00082 |

What is claimed is:

1. An apparatus for crimp-bonding multiple superposed plies of a fibrous cellulosic material comprising:

a rotating hardened metal crimp element and having machine direction and a cross-machine direction;

a rotating smooth hardened metal anvil element having a machine direction and a cross-machine direction;

protruding members configured on the surface of the crimp element in a discontinuous pattern aligned on an axis that is parallel to the cross-machine direction to provide a substantially continuous uniform area of localized surface contact between the rotating elements across the width of the plies; said protruding members being composed of individual elements arranged so that the surface area of an individual protruding member in contact with a fibrous cellulosic laminate between the rotating elements remains substantially constant as the crimp element rotates; and means to apply pressure against the rotating elements so that the pressure load on multiple plies of a fibrous cellulosic material at each area of localized surface contact is sufficient to form crimp bonds between the plies so the plies are joined by autohesive bonding.

2. The apparatus of claim 1, wherein the crimp element is a single hardened-metal pattern roll.

3. The apparatus of claim 1, wherein the crimp element is a series of hardened-metal pattern rolls.

4. The apparatus of claim 1, wherein the anvil element is a smooth, hardened-metal anvil roll.

5. The apparatus of claim 1, wherein the means to apply pressure is adapted to apply a pressure load on the multiple plies of fibrous cellulosic material between the rotating elements is greater than about 900 pounds per linear inch.

6. The apparatus of claim 1, wherein the means to apply pressure is adapted to apply a pressure load on the multiple plies of fibrous cellulosic material between the rotating elements is greater than about 1500 pounds per linear inch.

7. The apparatus of claim 1, wherein the means to apply pressure is adapted to apply a pressure load on the multiple plies of fibrous cellulosic material between the rotating elements is greater than about 2000 pounds per linear inch.

8. The apparatus of claim 1, wherein the means to apply pressure is adapted to apply a pressure so that the load between the rotating elements is greater than about 300 pounds of reactive force.

9. The apparatus of claim 1, wherein the crimp element has a width ranging from about 4 inches to about 160 inches.

10. The apparatus of claim 1, wherein the crimp element has a width ranging from about 4.5 inches to about 60 inches.

11. The apparatus of claim 1, wherein the crimp element has a width ranging from about 4.5 inches to about 12 inches.

12. An apparatus for crimp-bonding multiple superposed plies of a fibrous cellulosic material comprising:

a rotating hardened metal crimp element and having a machine direction and a cross-machine direction;

a rotating smooth hardened metal anvil element having a machine direction and a cross-machine direction;

protruding members configured on the surface of the crimp element in a discontinuous pattern aligned on an axis that is parallel to the cross-machine direction to provide a substantially continuous uniform area of localized surface contact between the rotating elements across the width of the plies, said protruding members being composed of individual elements arranged so that the surface area of an individual protruding member in contact with a fibrous cellulosic laminate between the rotating elements remains substantially constant as the crimp element rotates; and means to apply pressure against the rotating elements so that the pressure load on multiple plies of a fibrous cellulosic material at each area of localized surface contact is greater than about 900 pounds per linear inch to form crimp bond between the plies so the plies are joined by autohesive bonding.

13. The apparatus of claim 12, wherein the crimp element is a single hardened-metal pattern roll.

14. The apparatus of claim 12, wherein the crimp element is a series of hardened-metal pattern rolls.

15. The apparatus of claim 12, wherein the anvil element is a smooth, hardened-metal anvil roll.

16. The apparatus of claim 12, wherein the means to apply pressure is adapted to apply a pressure load on the multiple plies of fibrous cellulosic material between the rotating elements is greater than about 1500 pounds per linear inch.

17. The apparatus of claim 12, wherein the means to apply pressure is adapted to apply a pressure load on the multiple plies of fibrous cellulosic material between the rotating elements is greater than about 2000 pounds per linear inch.

18. The apparatus of claim 12, wherein the means to apply pressure is adapted to apply a pressure so that the load between the rotating elements is greater than about 300 pounds of reactive force.

19. The apparatus of claim 12, wherein the crimp element has a width ranging from about 4 inches to about 160 inches.

20. The apparatus of claim 12, wherein the crimp element has a width ranging from about 4.5 inches to about 60 inches.

* * * * *